(12) United States Patent
Weinstein et al.

(10) Patent No.: US 6,258,379 B1
(45) Date of Patent: *Jul. 10, 2001

(54) ANALGESIC DOSAGE UNITS FOR COORDINATED ADMINISTRATION

(76) Inventors: Robert Weinstein, 229 Berkeley St., Boston, MA (US) 02116; Allan Weinstein, 3301 New Mexico Ave., Washington, DC (US) 20016

(*) Notice: Subject to any disclaimer, the term of this patent is extended or adjusted under 35 U.S.C. 154(b) by 0 days.

This patent is subject to a terminal disclaimer.

(21) Appl. No.: 09/648,011

(22) Filed: Jul. 12, 1999

Related U.S. Application Data

(62) Division of application No. 08/901,702, filed on Jul. 28, 1997, now Pat. No. 6,077,530.

(51) Int. Cl.⁷ .............................. A61K 9/20; A61K 9/48
(52) U.S. Cl. ..................... 424/451; 424/441; 424/464; 424/455
(58) Field of Search ..................... 424/451, 441, 424/464, 455, 467, 456, 440, 468, 457

(56) References Cited

U.S. PATENT DOCUMENTS 6,077,530 * 6/2000 Weinstein et al. .................. 424/451

* cited by examiner

Primary Examiner—James M. Spear
(74) Attorney, Agent, or Firm—Bickel & Brewer

(57) ABSTRACT

A pharmaceutical dispensing kit that includes at least two different analgesic dosage units that have been formulated for use with each other, each of the analgesics being formulated for administration during a particular time of day and/or with relation to a particular event, the kit including a housing which contains said dosage units and which contains indicia identifying said dosage units and instructions coordinating use of the different dosage units together as a treatment regimen for pain. The dosage units may be packaged in bulk and distinguished by differences in geometry, size, markings, type of formulation (e.g., tablet versus soft gel capsule), and/or color, all types of indicia useful with this invention. A method for treating pain that uses the novel kit is also provided.

5 Claims, 2 Drawing Sheets

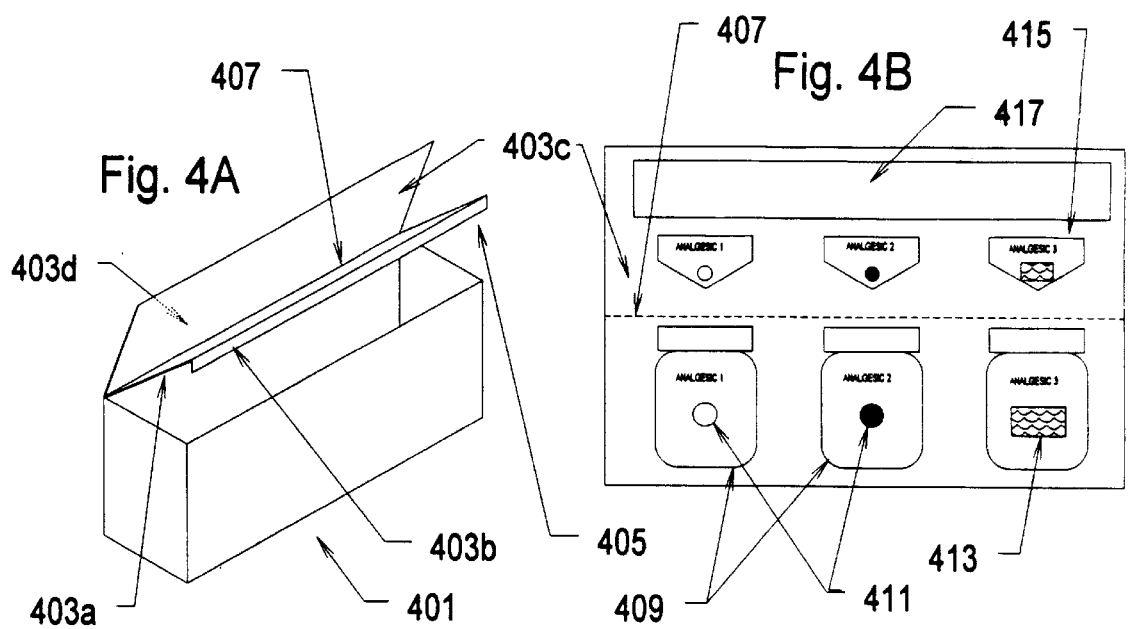
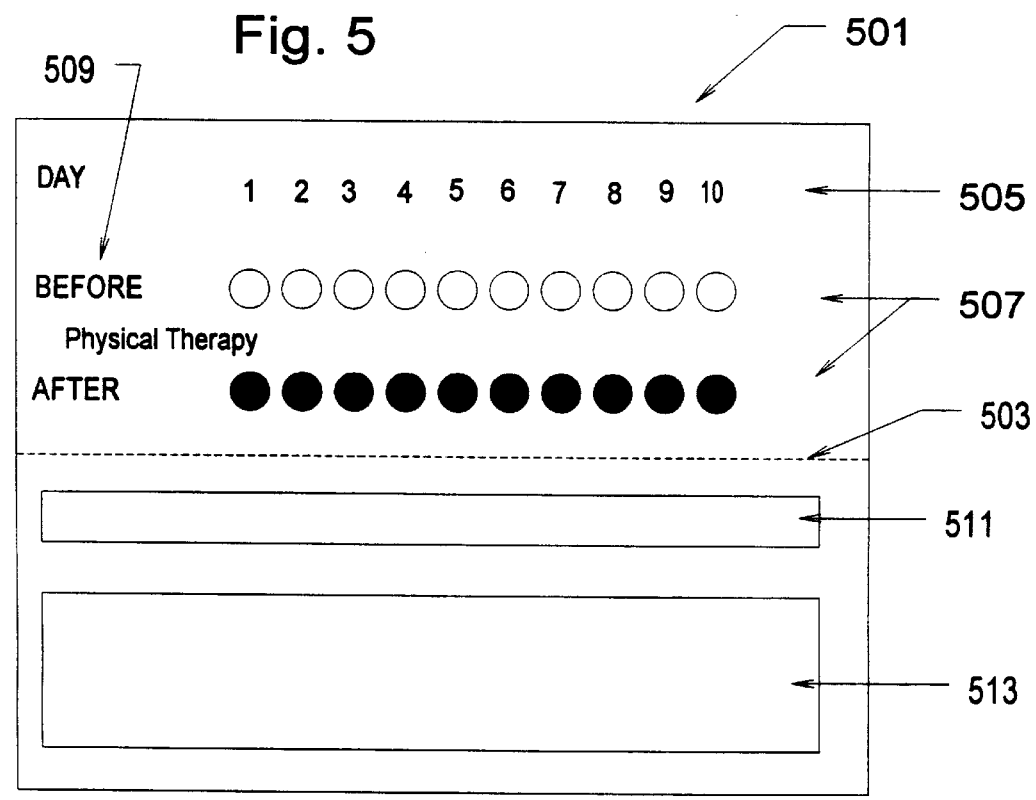

ANALGESIC DOSAGE UNITS FOR COORDINATED ADMINISTRATION

This application is a divisional of Ser. No. 08/901,702 filed Jul. 28, 1997, U.S. Pat. No. 6,077,530.

BACKGROUND OF THE INVENTION

1. The Field of the Invention

The present invention relates to an analgesic treatment regimen comprising different dosage units separately adapted for administration as a function of an event or the time of day, packaged with indicia for clarity of identification of the dosage units, and with instructions for use of the dosage units together in a pain treatment regimen. The invention also relates to packaging having both the different dosage units.

2. The State of the Art

Time of day and activity (or event) are important, and often overlooked, considerations in the management of pain. For example, pain can interfere with sleep, and continued sleep deficit or interruption can aggravate the patient's condition and sensitivity to pain, in addition to taking its toll on the patient's general welfare.

An analgesic medication having (or formulated to have) stimulant properties has drawbacks when sleep or sedation is desired, even though such a pharmaceutical preparation may be an otherwise effective formulation for pain. Many commercially available formulations contain caffeine (or other stimulants) because of its known synergistic effect with certain analgesic compounds. However, the instructions given for these medications may be devoid of any appreciation for problems relating to the administration of such medications when sleep or sedation is desired or necessary. Accordingly, patients taking such medications may suffer from irritability, insomnia, and/or sleeplessness, which they and/or their physician usually fail to attribute to the analgesic medication.

It is often the case that a sedative action is desired to facilitate the patient's sleep and recuperation. Certain analgesic formulations are inherently sedating (or are likely to cause drowsiness in patients). These compositions are most suitable for administration when sedation or sleep is desired or is not contraindicated. Conversely, sedation imposes a risk in individuals engaged in activities requiring cognitive acuity, such as in the operation of motor vehicles or machinery, and clinical studies have demonstrated diminished cognitive and motor performance associated with even minimally sedating analgesic medications, notably in subjects who are not aware of being impaired.

Unexpected side effects are especially likely with over-the-counter analgesic medications. In part, this problem is caused by consumer inattentiveness to the labelling, which lists ingredients, dosages, likely side effects, and other contraindications and warnings. Consumers typically do not analyze the package indicia and often rely on the brand name and the advertising dress on the packaging as a guide to self-prescribing. The appropriateness of taking a particular analgesic medication with regard to stimulation or sedation, or during the day, night, or both is not always readily apparent from the advertising dress. For example, Excedrin Extra Strength (available from Bristol-Myers Products, New York, N.Y.) would appear to be appropriate for administration during the day or night. However, this formulation contains 65 mg of caffeine, a stimulant, and so is inappropriate for nighttime use or when sleep or sedation is desired, although the dosing instructions do not so state. As another example, Bayer, Bayer Maximum Strength, and Bayer Select Maximum Strength would all appear suitable for day or night use, but the last one contains caffeine. As yet another example, Midol, Maximum Strength Midol, Multi-symptom Midol, Maximum Strength Multisymptom Midol, and Midol PMS would all appear suitable for day or night use; however, the second one listed contains caffeine and the last two contain an antihistamine having sedating effects. As still a further example, various medications for menstrual pain often contain a diuretic; taking such a medication before going to sleep can awaken the patient and reintroduce pain awareness, as well as rob the patient of necessary sleep because of the need to urinate, both due to the action of the diuretic.

The above-mentioned commercially available formulations are typical of the single entity medications, or medication formulations, presently sold over-the-counter or by prescription. None of these single dosage unit analgesic medications recommend use together with any other single dosage unit medication as a treatment regimen, nor do any of these single dosage unit analgesic medications contain instructions coordinating their use together with any other single dosage unit medication as a treatment regimen. All currently sold analgesic medications for relief of pain are single entity medications or single entity medication formulations which are available to a user either by over-the-counter sale or by prescription.

U.S. Pat. No. 3,515,265 discloses a unit dispenser for keeping track of the number of dosages of a particular medication which have or which are to be been taken.

U.S. Pat. No. 3,780,856 describes a device for use in hospitals to facilitate the administration of medications to a patients in which different medications are packaged in a 25×25 matrix of individual, detachable packages.

U.S. Pat. No. 4,038,937 describes a device for dispensing medications which includes a matrix of compartments correlated with indicia regarding the day of the week and the time of day the medication in a particular compartment is to be used.

U.S. Pat. No. 4,039,080 describes a tray for medicament pills having a matrix of compartments each associated with indicia regarding the day of the week and the time of day the medication in each compartment is to be taken.

U.S. Pat. No. 3,757,441 is directed to an article of manufacture for keeping a record of the times and days at which medicinal dosages are taken.

U.S. Pat. No. 4,295,567 (the disclosure of which is incorporated herein by reference) describes a medicament container for holding two dosage units which are symptomatic treatments for respiratory disorders, one dosage unit being indicated for daytime administration and being non-sedating, and the other dosage unit being indicated for nighttime administration and being sedating.

An important distinction should be drawn between analgesic medications and those used for treating respiratory disorders. Respiratory disorders pertain to the respiratory tract which includes the nasal passages, nasopharynx, bronchial tree, and pulmonary alveoli. Symptoms relating to these airways are primarily those of nasal congestion, sneezing, rhinorrhea, and post-nasal drip in the upper airways, and coughing, excess sputum production, wheezing, and shortness of breath, all associated with the lower airways. Medications for treating respiratory disorders therefore are those which reduce swelling of the respiratory passages, such as decongestants and antihistamines, those which decrease smooth muscle constriction such as xanthene bronchodilators, and those which facilitate mucous flow, such as mucolytics which thin secretions. These medications for treating respiratory disorders have no mode of action known to be associated with blocking the transmission or perception of pain, and so would not be considered useful in the treatment of tension or migraine headache, musculoskeletal pain such as present in backache and osteoarthritis, menstruation-related pain, or the pain of rheumatologic disorders.

Pain treatment for headache, musculoskeletal pain, menstruation-related pain, and rheumatologic disorders could be made more effective if medications that were primarily analgesic in nature were formulated to achieve additional therapeutic objectives, such as (i) reduction of anxiety, (ii) diuresis, (iii) vasoconstriction, (iv) reduction of inflammation, (v) relaxation of skeletal muscles, and/or (vi) induction of sleep in order to enhance the analgesic effect. Formulation of such analgesic compositions having multiple active ingredients used together requires careful appreciation of the individual and cumulative properties of the ingredients. A lay consumer choosing individual components is unlikely to achieve maximal therapeutic success and could risk harm from inappropriate dosing and unwanted side effects. The lay consumer choosing a multiplicity of dosage units for use together would have to glean information by muddling through a significant amount of fine print, the location and arrangement of which differs on the packages and/or inserts of the various analgesic manufacturers, to achieve the desired effect. Likewise, administration of a multiplicity of prescription medications suffers from a lack of coordinated dosing due to separate packaging and separate instructions for each medication. Thus, administration of multiple medications can result in incompatibility so that the desired analgesic effects are not achieved or so that the patient's condition is aggravated rather then relieved. Moreover, the use of multiple and various configured medications and packaging provide an increased risk of confusion, medication error, and lack of compliance.

SUMMARY OF THE INVENTION

Accordingly, it is the principal object of the present invention to provide a treatment for pain by providing a combination of medications particularly adapted for administration with regard to time of day and/or a particular event and organized via packaging and/or indicia for use together in a treatment regimen. Among the benefits achieved are improving the patient's therapy, and avoiding unwanted side effects inherent in taking the same medication for all activities and events, and avoiding the risks of taking a multiplicity of uncoordinated medications.

In brief, the present invention provides a combination of separately formulated dosage units which together are effective for the treatment of pain, the dosage units being formulated so as to be adapted for administration during separate events or times of day. The present invention provides a pharmaceutical housing that contains a combination of at least two dosage units for use together, each of which is effective for the treatment of pain, one type of dosage unit being adapted for administration during one time of day or for a particular event, and the other type of dosage unit being adapted for administration during a different time of day or for a different event. The housing and/or the dosage units have indicia for distinguishing the different types of dosage units from each other, and the housing contains dosing instructions for administration of the different types of dosage units together in a pain treatment regimen.

BRIEF DESCRIPTION OF THE DRAWINGS

FIG. 4A depicts a perspective of a package having a plurality of analgesic medications to be dosed at separate times of day or for separate events, like dosage units being protected together in bottles, indicia for distinguishing the dosage units from each other, and instructions for dosing information;

FIG. 4B depicts a more detailed view of the indicia on the cover of the package.

FIG. 5 depicts an analgesic regimen with capsules/tablets packaged on a card.

DETAILED DESCRIPTION OF SPECIFIC EMBODIMENTS

Figure 1:
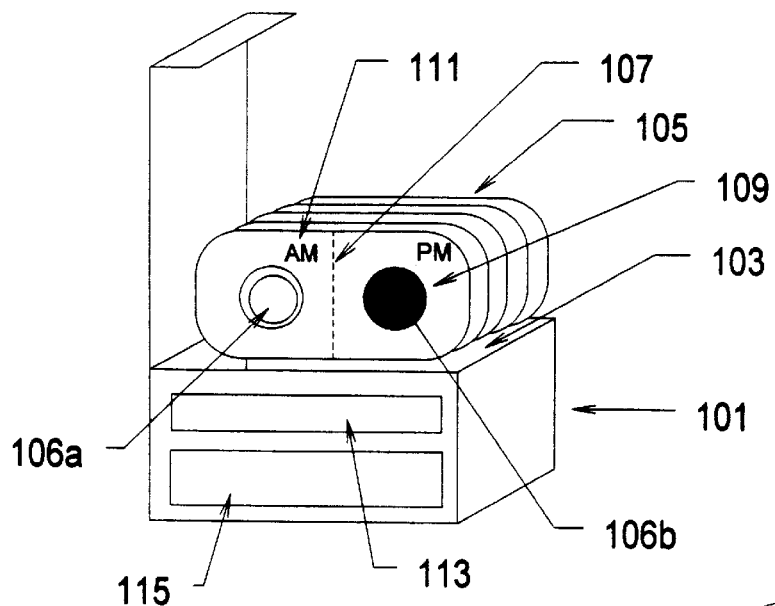
FIG. 1 depicts an idealized preferred dosage kit having multiple daily two dose blister cards, each containing one dosage unit for administration during the day and one for taking at night, and indicia for distinguishing the two dosage units, and instructions for their coordinated administration in a pain treatment regimen.

The present invention provides a kit containing at least two analgesic dosage units for the treatment of pain. One dosage unit is designed to be administered during a particular time of day or with relation to a particular event, and the other is formulated for administration during a different time of day or with regard to a different event or having a different relation to the same event.

As used herein, an "event" relates to a symptom, such as backache or headache, and/or the patient's desire to participate in a particular activity or action, such as working, sleeping, reading, driving, eating, and the like. Although the event of going to sleep is assumed to occur during the night, shift workers, physicians and nurses, and others may not have a schedule which allows them to sleep at night and work during the normal business hours.

As used herein, a "dosage unit" is a pharmaceutical composition or formulation comprising at least one ingredient providing analgesic effects and optionally another ingredient. Preferably the dosage unit is unitary, such as a single pill or liquid, containing all of the desired active ingredients and the inactive ingredients necessary and desired for making a dosage suitable for administration (e.g., tabletting compounds such as binders, fillers, and the like); the dosage unit can consist of a number of different dosage forms (e.g., pill(s) and/or liquid(s)) designed to be taken simultaneously as a dosage unit.

In the treatment of simple headaches, musculoskeletal and rheumatologic disorders, menstrual cramps, sports and similar injuries, dental pain, and the like, existing pharmaceutical therapies have a single type of dosage unit for relief of the symptom(s). According to this invention, at least two different types of dosage units are provided, each of which comprises a pharmaceutically effective amount of an ingredient providing analgesic effects, which may be the same or different in each formulation, and the dosage units are formulated specifically to an event before, during, or after which, or time of day during which, the particular dosage unit is administered.

It should be understood within the context of this invention that an "analgesic" can take a number of different forms.

Typically as used herein, analgesics are agents that block pain perception through neurological pathways, such as acetaminophen and acetylsalicylic acid (aspirin, which also has antiinflammatory effects), both considered non-narcotic; propyxphene HCl, codeine, and meperidine (all three considered to be narcotics). In this invention, each of the novel dosage units will have at least one analgesic as, for example, that term is used in The Merck Index (Rahway, N.J.: Merck & Co., 1989); examples of analgesics in addition to those now sold over the counter include codeine and derivatives and related compounds (e.g., dihydrocodeine, dihydromorphine, and hydrocodone), fentanyl, meperidine, properidine, acetanilide, etodolac, fenoprofen, indomethacin, and the like.

As noted above, analgesia can be facilitated by formulating the dosage unit to include, in addition to an analgesic, at least one ingredient that reduces anxiety, causes diuresis, causes vasoconstriction, reduces inflammation, relaxes skeletal muscles, causes stimulation, and/or induces sleep.

Additives that induce vasoconstriction, such as caffeine or isometheptene, act to induce cranial vasoconstriction and so reduce the pain of headaches, but can also cause stimulation, irritability, and insomnia.

Additives that induce diuresis are useful for the treatment of PMS and menstrual disorders where fluid retention is an aggravating factor in causing pain. Examples include caffeine, pamabrom, and thiazides, the former of which can also cause stimulation and insomnia. Diuresis is preferentially or preferably induced only during the daytime or when the patient will not be sleeping, as promoting urination when the patient is likely to be asleep is likely to cause the patient to awaken to urinate, thus reducing needed sleep.

Additives that reduce the patient's emotional reaction to pain, especially by sedation or hypnotics, such as butalbital (a barbiturate), dichloralphenazone (in Midrin 100 mg), phentoloxamine, and anxiolytic medication (such as diazepam), can be useful in the treatment of pain by alleviating the patient's concentration or focus on the pain.

Other additives facilitate alleviating the pain of musculoskeletal disorders, muscle tension, contraction, and spasms. These types of muscle relaxing additives include methocarbalol, diazepam, and orphenadrine; the first two often have sedating effects, and the last one can induce caffeine-like stimulatory side effects. Thus, these muscle relaxants can be formulated with the analgesic to provide a sedative or a stimulatory effect if one is desired.

Finally, anti-inflammatory components facilitate pain treatment by alleviating the painful inflammatory component of disorders such as osteoarthritis, rheumatoid arthritis, ankylosing spondylitis, bursitis, and tendinitis. Examples of non-steroidal anti-inflammatory drugs (NSAIDs) include salicylates, ibuprofen, indomethacin, and naproxen (e.g., sodium salt). Side effects of these active ingredients include fluid retention and drowsiness (such as with naproxen sodium), another formulation problem unappreciated by existing products.

It may be desirable to facilitate the self-administration of the formulation desired for use during waking hours by adding a mild stimulant to the dosage unit. Suitable stimulant additives include caffeine, pseudoephedrine, and phenylpropanolamine, and compatible and safe mixtures thereof. The presence of a stimulant in the dosage unit when sedation or sleep is not contraindicated is often beneficial for headache relief and the counteract the fatigue typically accompanying chronic pain.

For a dosage unit desired for use when sedation or sleep is not contraindicated, or is desirable (e.g., because of lack of sleep due to pain), it is preferred to use a sedating analgesic or the same analgesic as used in the non-sedating dosage unit in combination with a mild sedative or sedating ingredient(s). Suitable sedatives include diphenhydramine, diazepam, methaqualude, and butalbarbatal. Accordingly, this type of dosage unit provides the added benefit of being sedating, which can synergistically aid in the relief of pains and aches. Additionally, the known (or at least suspected) benefits of sleep and relaxation on pain can be enhanced by the use of a sedating formulation given when sedation is desired.

The two or more dosage units can be packaged together in a kit, as shown in the figures. FIG. 1 depicts a perspective view of a package kit according to this invention, in which a housing 101, shown as a conventional paper or paperboard box, is provided with a receptacle 103 for retaining each of the separate dosage units designed for use together. As shown, the housing holds a number of dual-dosage unit blister cards 105 (e.g., foil backed) each having two dosage units 106a/b and a score line 107 separating the two units. Blister cards allow for the dosage units to be packaged individually protected; analogous. The dosage unit or the plastic blister in which it resides can be colored or tinted to further identify the time or event prompting when the dosage unit should be taken; for example, a dosage unit to be taken at night can-be identified by a dark circle 109 printed on the backing and viewable through the blister or on the plastic blister. The optional shading or coloring can be associated with or replaced by indicia 111 on the blister card that indicates the time or event prompting administration. The outside of the housing preferably includes indicia 113 for identifying the particular dosage units packaged in the housing, as well as instructions 115 to coordinate their use together in a combined pain treatment regimen.

Figure 2:
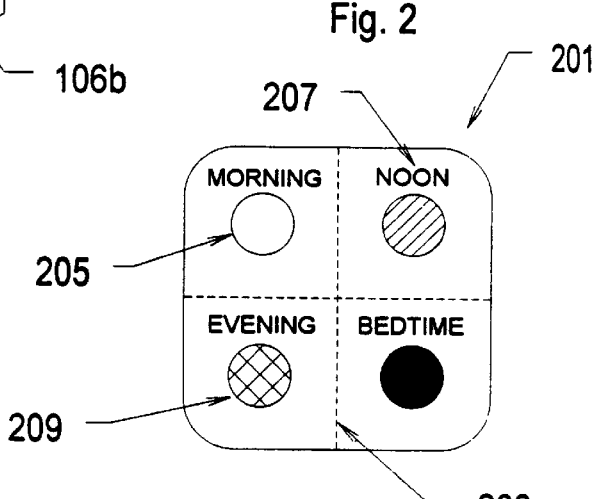
FIG. 2 depicts a daily four dose blister card.

FIG. 2 depicts a daily four dosage unit blister card 201 having score lines 203 dividing the preferably rectangular blister pack into four quadrants, each quadrant including a blister 205 in which a dosage unit is housed. Each quadrant preferably has at least one of printed indicia 207 and/or graphical/colored indicia 209 for distinguishing the dosage units.

Figure 3:
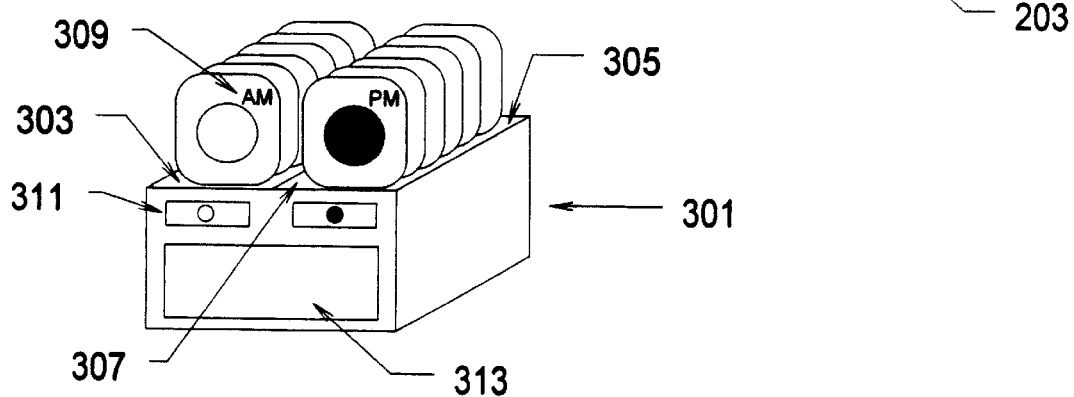
FIG. 3 depicts a kit containing individually protected dosage units, the housing and the protected dosage units having some indicia for distinguishing the different dosage units, and instructions for coordinating their administration.

The embodiment shown in FIG. 3, analogous to that shown in FIG. 1, has a housing 301 with receptacles 303 and 305 defined by optional partition 307 for separating the two time-dependent dosage units. As shown, the physical dosage units are divided by the partition into those for administration during the daytime and those for administration during the nighttime. The time of administration can be further indicated by the textual indicia 309 on the unit dosage unit pack, by coloring or shading as shown in FIG. 2, and/or by additional graphical indicia 311 on the housing. The outside of the housing preferably also includes textual instructions 313 regarding the time of day during which each of the particular dosage units is to be taken in order to follow a pain treatment regimen. The areas enclosed by each of the partitions can be of different sizes (volumes), which may be desirable when a different quantity of unit dosages of each formulation is needed for the daytime administration.

FIG. 4A depicts a perspective view of a housing 401 having a structure providing for prescribing indicia thereon. The housing (shown as a paper, paperboard, or cardboard box) can be made conventionally from a single folded and glued piece of paper (or paperboard or cardboard). The portion of the single piece defining the closable lid 403 is first folded conventionally to provide a conventional lid 403a with a tab 405 for inserting into the box interior, then folded back upon itself to provide an overlapping portion 403b effectively doubling the lid 403a, then folded up to provide a flap 403c, and then again back upon itself doubling the flap 403d. The composite, doubled lid has a fold or score line 407 so that the flap can be folded onto and then secured overlying the lid (such as with tamper-proof tape) so that the container has the configuration of a rectangular solid. FIG. 4B depicts an example of the indicia seen on the abutting flap and cover surfaces (403b and 403c) when opened. The graphical indicia can include pictures of bottles (e.g., 409), preferably corresponding to the shape and color of those in the housing, and each bottle can also include indicia 411 about the color and/or shape of dosage units (e.g., tablets, pills, or capsules) in the bottles, and preferably a different indicium 413 signifying that the associated bottle contains a liquid medication. The flap preferably includes other indicia 415 identifying the dosage unit containers and the dosage units therein, and also has a place 417 for more detailed instructions about coordinated administration of the dosage units in the housing to achieve a pain treatment regimen. Bottles are a preferred manner of protecting like dosage units together.

FIG. 5 depicts a single treatment card having a prescribed regimen of ten days' pain treatment; again, this card can be a blister pack. The pack 501, preferably made of paperboard, can be provided with a score line 503 for folding and sealing. Each of the days of treatment 505 (ten in this example) is indicated textually and/or graphically. The tablets (here a dual dosage, one for administration one hour before physical therapy, and one for administration two hours after physical therapy) can be blister-packed adjacent to the day of treatment indicia with graphical and/or textual indicia 509 indicating the time during which the particular dosage unit(s) should be taken. As with the above examples, the plastic and/or the tablet can be color-coded to enhance compliance with the time or event prompting when a particular dosage unit should be taken. The other part of the blister card preferably includes other indicia 511, analogous to that 415 in FIG. 4B, distinguishing the types of dosage units on the card, and also instructions 513 for coordinated administration of all of the dosage units on the card in order to achieve a pain treatment regimen. An advantage to using packaging arrangements where all of the discrete dosage units are visible to inspection is the further indication whether any particular dosage has been taken or missed.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets or the like, as shown in the present figures. The dosage units may further include conventional excipients well-known in pharmaceutical formulation practice, such as binding agents, gellants, fillers, tabletting lubricants, disintegrants, surfactants, and colorants; and for suckable or chewable formulations.

When bulk containers such as bottles or the blister cards shown in the figures are used for housing and dispensing the different event/time-of-day formulations, the individual dosage units for administration during one time of day (or before or during or after a given event) can be physically distinguishable from those for administration at another time or event. The dosages may be provided with user-discernable differences in geometry, size, color, texture, and/or markings, and the like, and combinations thereof.

Preferably, there is additional indicia accompanying the product that clearly indicates to the user the distinguishing characteristics of the various dosage units, the time or event triggering when each is to be taken, and instructions for the coordinated administration of the various dosage units for achieving a pain treatment regimen. For example, the housing or product literature or can provide coordinated instructions that the patient is to "take one red tablet twice during the day and take one blue tablet once at bedtime" or "take one red [stimulating] tablet in the morning, a green [non-sedating, non-stimulating] tablet in the middle of the afternoon, and a blue [sedating] tablet at bedtime." Likewise, the medications can be distinguished as different types of formulations; for example, a lozenge or capsule for one particular administration and a tablet or pill for the other time of administration.

Thus, in a preferred embodiment the invention provides a housing and dosage unit containers having means for distinguishing between the various dosage units, and further including coordinated instructions for administering each of the various types of dosage units to achieve a treatment for pain, wherein the various types of dosage units are formulated for administration at different times and/or with reference to different events. The means for distinguishing between the two or more types of formulations can include, for example, one or a combination of: separate receptacles; different physical aspects (e.g., color, shape, size, etc.); different placement of the formulations in the housing (e.g., a particular place on a blister pack); and the like.

Other examples of coordinated dosage units are provided below. In connection with the following examples, it should be apparent that these combinations as described are generally based on active ingredients existing in currently marketed products.

Comparative Example 1

A single entity analgesic medication and dosage:

| Time | Dosage Unit Ingredient(s) | Dose |
|---|---|---|
| AM | acetaminophen 325 mg | 2 |
| NOON | acetaminophen 325 mg | 2 |
| EVENING | acetaminophen 325 mg | 2 |
| BEDTIME | acetaminophen 325 mg | 2 |

EXAMPLE 1

Dual entity analgesic regimen for daytime diuresis:

| Time | Dosage Unit Ingredient(s) | Dose |
|---|---|---|
| AM | acetaminophen 325 mg + pamabrom 25 mg | 2 |
| NOON | acetaminophen 325 mg + pamabrom 25 mg | 2 |
| EVENING | acetaminophen 325 mg + pamabrom 25 mg | 2 |
| BEDTIME | acetaminophen 325 mg | 2 |

EXAMPLE 2

Dual entity analgesic regimen for nighttime sedation:

| Time | Dosage Unit Ingredient(s) | Dose |
| --- | --- | --- |
| AM | acetaminophen 325 mg | 2 |
| NOON | acetaminophen 325 mg | 2 |
| EVENING | acetaminophen 325 mg | 2 |
| BEDTIME | acetaminophen 325 mg + butalbital 50 mg | 2 |

EXAMPLE 3

Analgesic regimen that achieves daytime diuresis and nighttime sedation:

| Time | Dosage Unit Ingredient(s) | Dose |
| --- | --- | --- |
| AM | acetaminophen 325 mg + pamabrom 25 mg | 2 |
| NOON | acetaminophen 325 mg + pamabrom 25 mg | 2 |
| EVENING | acetaminophen 325 mg + pamabrom 25 mg | 2 |
| BEDTIME | acetaminophen 325 mg + butalbital 50 mg | 2 |

EXAMPLE 4

Triple entity analgesic regimen that achieves daytime cranial vasoconstriction, evening and nighttime sedation, and avoid nighttime stimulation (butalbital counteracts the stimulating effects of caffeine taken before bedtime):

| Time | Dosage Unit Ingredient(s) | Dose |
| --- | --- | --- |
| AM | aspirin 325 mg + caffeine 30 mg | 2 |
| NOON | aspirin 325 mg + caffeine 30 mg | 2 |
| EVENING | aspirin 325 mg + caffeine 30 mg + butalbital 50 mg | 2 |
| BEDTIME | aspirin 325 mg + butalbital 50 mg | 2 |

EXAMPLE 5

A triple entity analgesic that achieves daytime cranial vasoconstriction, skeletal muscle relaxation, and reduction of anxiety, and nighttime sedation:

| Time | Dosage Unit Ingredient(s) | Dose |
| --- | --- | --- |
| AM | acetaminophen 325 mg + caffeine 30 mg + diazepam 2 mg | 2 |
| NOON | acetaminophen 325 mg + caffeine 30 mg + diazepam 2 mg | 2 |
| EVENING | acetaminophen 325 mg + caffeine 30 mg + diazepam 2 mg | 2 |
| BEDTIME | acetaminophen 325 mg + diazepam 5 mg | 2 |

EXAMPLE 6

A dual entity analgesic regimen that is antiinflammatory and in which the sedation and fluid retention associated with the antiinflammatory analgesic is counteracted by formulation during the day:

| Time | Dosage Unit Ingredient(s) | Dose |
| --- | --- | --- |
| AM | naproxen sodium 375 mg + caffeine 60 mg | 1 |
| Bedtime | naproxen sodium 375 mg + diazepam 5 mg | 1 |

EXAMPLE 7

A dual entity analgesic regimen for a patient in pain and undergoing a regimen of physical therapy, for administration related to when the physical therapy session is conducted, comprises:

| Time | Dosage Unit Ingredient(s) | Dose |
| --- | --- | --- |
| Before Physical Therapy (PT) | aspirin 375 mg + caffeine 30 mg | 2 -- 2 hrs before PT |
| After Physical Therapy | aspirin 375 mg + diazepam 5 mg | 2 -- 2 hours after PT |

The foregoing description is meant to illustrate the invention to the average artisan, and various changes and additions may become apparent upon a review of this specification. Such modifications are intended to be within the scope and spirit of the invention as defined by the following claims.

What is claimed is:

1. A pharmaceutical kit for treating pain associated with simple and migraine headache, musculoskeletal pain and backache, menstruation, rheumatologic inflammation, sports injury, and dental disorders comprising:

a first analgesic dosage unit;

a second analgesic dosage unit, wherein said first but not said second dosage unit contains a diuretic agent;

indicia distinguishing said first and second dosage units from each other;

instructions for coordinating the administration of each of said first and second analgesic dosage units as an analgesic treatment regimen whereby said first dosage unit is for administration during a particular time of day or event when diuresis is desired and the side effect(s) of said diuretic agent is not contraindicated; and a container which incorporates a plurality of said first and second analgesic dosage units, said indicia and said instructions.

2. A pharmaceutical kit for treating pain associated with simple and migraine headache, musculoskeletal pain and backache, menstruation, rheumatologic inflammation, sports injury and dental disorders comprising:

a first analgesic dosage unit;

a second analgesic dosage unit, wherein said first but not said second dosage unit contains a vasoconstricting agent;

indicia distinguishing said first and second dosage units from each other;

instructions for coordinating the administration of each of said first and second dosage units as an analgesic treatment regimen whereby said first dosage unit is for administration during a particular time of day or event when vasoconstriction is desired and the side effect(s) of said vasoconstricting agent is not contraindicated; and a container which incorporates a plurality of said first and second analgesic dosage units, said indicia and said instructions.

3. A pharmaceutical kit for treating pain associated with simple and migraine headache, musculoskeletal pain and backache, menstruation, rheumatologic inflammation, sports injury and dental disorders comprising:

a first analgesic dosage unit;

a second analgesic dosage unit, wherein said first but not said second dosage unit contains a skeletal muscle relaxing agent;

indicia distinguishing said first and second dosage units from each other;

instructions for coordinating the administration of each of said first and second analgesic dosage units as an analgesic treatment regimen whereby said first dosage unit is for administration during a particular time of day or event when muscle relaxation is desired and the side effect(s) of said skeletal muscle relaxing agent is not contraindicated; and a container which incorporates a plurality of said first and second analgesic dosage units, said indicia and said instructions.

4. A pharmaceutical kit for treating pain associated with simple and migraine headache, musculoskeletal pain and backache, menstruation, rheumatologic inflammation, sports injury and dental disorders comprising:

a first analgesic dosage unit;

a second analgesic dosage unit, wherein said first but not said second dosage unit contains a stimulant;

indicia distinguishing said first and second dosage units from each other;

instructions for coordinating the administration of each of said first and second analgesic dosage units as an analgesic treatment regimen whereby said first dosage unit is for administration during a particular time of day or event when stimulation is desired and the side effect(s) of said stimulant is not contraindicated; and a container which incorporates a plurality of said first and second analgesic dosage units, said indicia and said instructions.

5. A pharmaceutical kit for treating pain associated with simple and migraine headache, musculoskeletal pain and backache, menstruation, rheumatologic inflammation, sports injury and dental disorders comprising:

a first analgesic dosage unit;

a second analgesic dosage unit, wherein said first but not said second dosage unit contains an anxiolytic agent;

indicia distinguishing said first and second dosage units from each other;

instructions for coordinating the administration of each of said first and second analgesic dosage units as an analgesic treatment regimen whereby said first dosage is unit for administration during a particular time of day or event when reduction of anxiety is desired and the side effects of said anxiolytic agent is not contraindicated; and a container which incorporates a plurality of said first and second analgesic dosage units, said indicia and said instructions.

* * * * *